United States Patent [19]

Ross et al.

[11] Patent Number: 5,648,076
[45] Date of Patent: Jul. 15, 1997

[54] INHIBITION OF VASCULAR STENOSIS

[75] Inventors: Russell Ross; Michael A. Reidy; Elaine W. Raines; Volkhard Lindner, all of Seattle, Wash.; Gordon A. A. Ferns, Brentwood, Great Britain

[73] Assignee: Board of Regents of University of Washington, Seattle, Wash.

[21] Appl. No.: 281,132

[22] Filed: Jul. 26, 1994

Related U.S. Application Data

[63] Continuation of Ser. No. 641,758, Jan. 17, 1991, abandoned.
[51] Int. Cl.$^6$ .......................... A61K 39/395; C07K 16/22
[52] U.S. Cl. ...................... 424/145.1; 424/158.1; 530/387.1; 530/388.24; 530/389.2
[58] Field of Search ........................ 424/158.1, 145.1; 530/389.2, 388.24

[56] References Cited

U.S. PATENT DOCUMENTS 5,268,358  12/1993  Fretto .......................................... 514/12

FOREIGN PATENT DOCUMENTS 288687     11/1988  European Pat. Off. ......... C12P 21/00
327369      9/1989  European Pat. Off. ......... C12N 15/00
WO91/06668  5/1991  WIPO ............................. C12P 21/08

OTHER PUBLICATIONS

Harker Am. Journal of Cardiology Jul. 1987 60(3) 20B–28B.
Hart et al. J. Biological Chem 1987 262(22) 10780.
Rubin et al., "Induction of B–Type Receptors for Platelet–Derived Growth Factor in Vascular Inflammation: Possible Implications for Development of Vascular Proliferative Lesions", *Lancet*, 1[8599]:1353–1356, 1988.
G.A.A. Ferns et al., "Inhibition of Neointimal Smooth Muscle Accumulation After Angioplasty by an Antibody to PDGF", *Science* 253:1129–1132.

V. Lindner et al., "Proliferation of Smooth Muscle Cells After Vascular Injury is Inhibited by an Antibody Against Basic Fibroblast Growth Factor", *Proc. Natl. Acad. Sci. USA* 88: 3739–3743, 1991.

R. Ross et al., "Localization of PDGF–B Protein in Macrophages in All Phases of Atherogenesis", *Science* 248: 1009–1012, 1990.

U.S. application No. 07/365,715 La Rochelle et al., filed Jun. 14, 1989.

Kraiss et al., "Regional Expression of the Platelet–derived Growth Factor and Its Receptors in a Primate Graft Model of Vessel Wall Assembly," *J. Clin. Invest. 92:338–348,* 1993.

Hart et al., "Purification of PDGF–AB and PDGF–BB from Human Platelet Extracts and Identification of All Three PDGF Dimers in Human Platelets," *Biochem 29:166–172,* 1990.

Raines et al., "Compartmentalization of PDGF on Extracellular Binding Sites Dependent on Exon–6–Encoded Sequences," *J. Cell Biol. 116(2):533–543,* 1992.

*Primary Examiner*—Lila Feisee
*Assistant Examiner*—Nancy A. Johnson
*Attorney, Agent, or Firm*—Seed and Berry LLP

[57] ABSTRACT

Methods for inhibiting vascular stenosis in a mammal, including restenosis following surgical removal of atherosclerotic plaques. Inhibition is achieved through the administration of anti-growth factor antibodies, including anti-FGF antibodies and anti-PDGF antibodies.

20 Claims, 2 Drawing Sheets

INHIBITION OF VASCULAR STENOSIS

CROSS-REFERENCE TO RELATED APPLICATION

This application is a continuation of U.S. patent application Ser. No. 07/641,758, filed Jan. 17, 1991, now abandoned.

Development of this invention was supported in part by National Institutes of Health Grants 1P50HL 42270-01, HL 03174-35, HL 41103 and HL 18645. The Government may have certain rights in this invention.

TECHNICAL FIELD

The present invention relates to methods for inhibiting stenosis in a mammal following vascular injury, and to compositions useful within those methods.

BACKGROUND OF THE INVENTION

Proliferation of smooth muscle cells (SMCs) in the vessel wall is an important event in the formation of vascular lesions in atherosclerosis or in response to vascular injury. Treatment of atherosclerosis frequently includes the clearing of blocked vessels by angioplasty or endartarectomy, surgical procedures in which atherosclerotic plaques are compressed or removed through catheterization (angioplasty) or stripped away from the arterial wall through an incision (endartarectomy). These procedures remove the vascular endothelium, disturb the underlying intimal layer, and result in the death of medial SMCs. This injury is followed by medial SMC proliferation and migration into the intima, which characteristically occurs within the first few weeks after injury and stops when the overlying endothelial layer is reestablished.

In about 30% or more of patients treated by angioplasty or endartarectomy, thrombosis and/or SMC proliferation in the intima causes re-occlusion of the vessel and consequent failure of the angioplasty or endartarectomy. This closure of the vessel subsequent to surgery is known as restenosis.

A similar process of SMC proliferation has also been observed in vascular grafts and organ transplants, and may contribute to transplant rejection.

It has been postulated that growth factors, such as platelet derived growth factor (PDGF), play a role in the development of atherosclerotic plaques (reviewed by Ross et al., Cell 46: 155–169, 1986). One proposed mechanism for plaque formation is the release by platelets, at sites of endothelial denudation, of growth factors that stimulate SMC growth (Ross and Glomset, N. Eng. J. Med. 295: 369–377, 420–425, 1976; Ross, Arteriosclerosis 1: 293–311, 1981). Moore et al. (Thrombos. Haemostas. (Stuttg.) 35: 70, 1976) and Friedman et al. (J. Clin. Invest. 60: 1191–1201, 1977), using an indwelling catheter injury model, reported an inhibition of experimentally induced intimal lesion formation in rabbit arteries by prolonged thrombocytopenia induced by administration of anti-platelet serum. It has also been postulated that SMCs may themselves produce PDGF which stimulates lesion development through an autocrine mechanism (Ross et al., ibid; Walker et al., Proc. Natl. Acad. Sci. USA 83: 7311–7315, 1986). Fingerle et al. (P roco Natl. Acad. Sci. USA 86: 8412–8416, 1989) investigated intimal lesion formation in thrombocytopenic rats and concluded that platelets do not play a role in the initial SMC proliferation after balloon injury but may regulate SMC migration into the intima. Platelets are now known to release a number of growth factors, including PDGF, transforming growth factors alpha and beta (TGFα and TGFβ), insulin-like growth factor I (IGF-I) and platelet derived endothelial cell growth factor. However, there has been no direct evidence to demonstrate that a particular mitogen or mitogens is responsible for the development of arterial lesions.

Removal of atherosclerotic plaques by angioplasty or endartarectomy has limited efficacy, and no effective treatment for restenosis has been developed. There is therefore a need in the art for methods of reducing or preventing stenosis of blood vessels following vascular injury, such as injury due to balloon catheterization or endarterectomy, as well as in vascular grafts and organ transplants. The present invention provides such methods and fulfills other, related needs.

DISCLOSURE OF THE INVENTION

The present invention provides methods for inhibiting vascular stenosis, including restenosis following angioplasty, endarterectomy or other procedures whereby atherosclerotic plaques are removed from blood vessels. These methods generally comprise administering to a mammal an anti-growth factor antibody in an amount sufficient to inhibit mitogenesis and/or migration of smooth muscle cells. Within preferred embodiments, the antibody is an anti-fibroblast growth factor antibody or an anti-platelet derived growth factor antibody. Monoclonal antibodies are preferred.

In a related aspect, the present invention provides methods for inhibiting restenosis in a mammal following angioplasty or endarterectomy comprising administering to the mammal an anti-growth factor antibody in an amount sufficient to inhibit restenosis. Anti-fibroblast growth factor antibodies and anti-platelet derived growth factor antibodies may be used. In one embodiment, the antibody is administered prior to angioplasty or endarterectomy. In another embodiment, the antibody is administered subsequent to angioplasty or endarterectomy. In yet another embodiment, a panel of anti-growth factor antibodies is used, such as a panel of antibodies capable of neutralizing the AA, AB and BB isoforms of platelet derived growth factor.

Another aspect of the invention provides a method of inhibiting restenosis following angioplasty or endarterectomy, wherein an anti-fibroblast growth factor antibody is administered to a mammal prior to angioplasty or endarterectomy in an amount sufficient to inhibit restenosis, and an anti-platelet derived growth factor antibody is administered to the mammal subsequent to angioplasty or endarterectomy in an amount sufficient to inhibit restenosis.

These and other aspects of the invention will become evident upon reference to the following detailed description and the attached drawings.

DETAILED DESCRIPTION OF THE INVENTION

Figure 1:
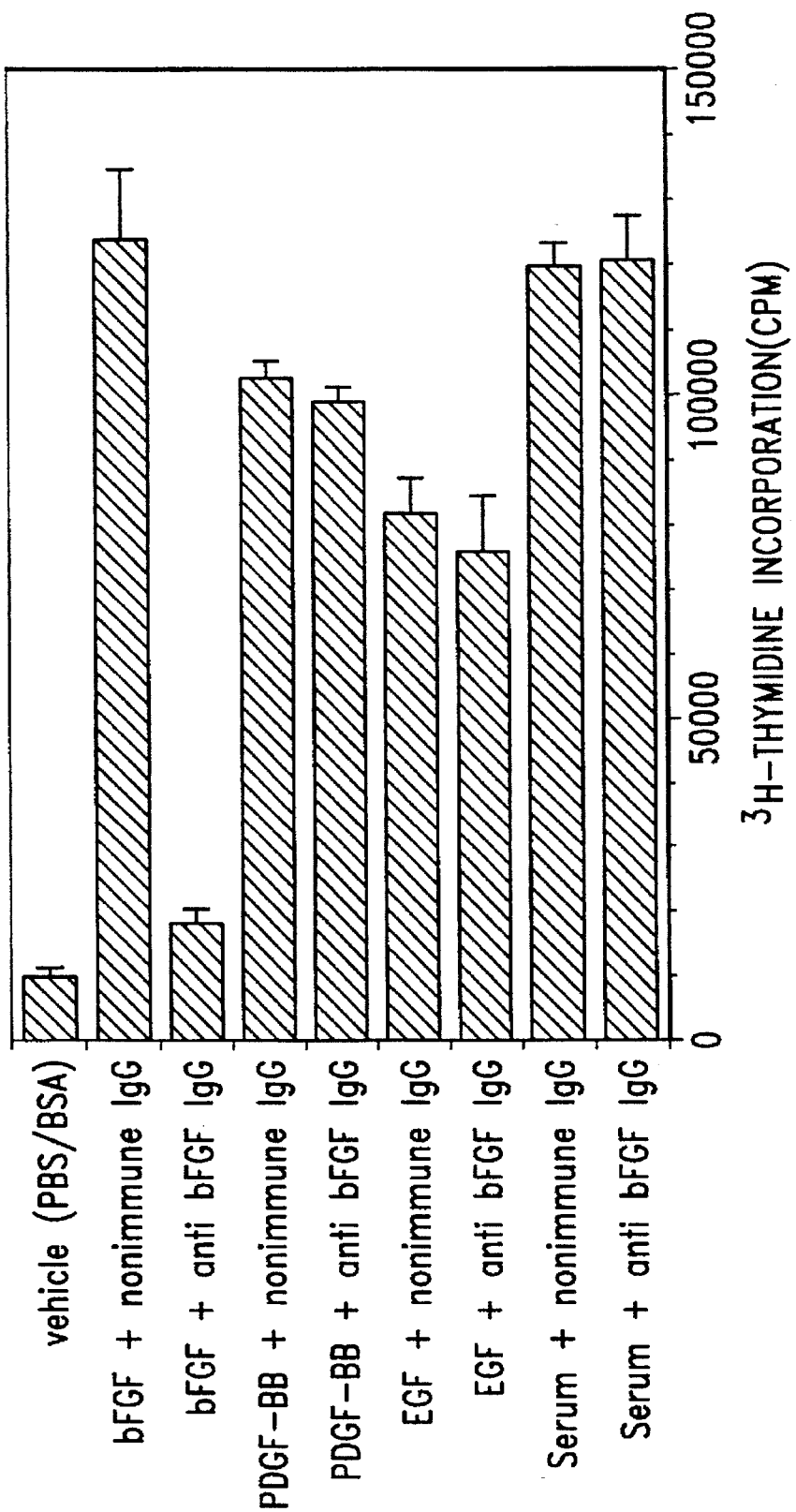
FIG. 1 illustrates the effect of an anti-bFGF antibody on proliferation of 3T3-D1 cells in response to 5 ng each of bFGF, PDGF-BB and EGF, and to calf serum (5%).

As noted above, restenosis of blood vessels is a common problem in patients who have undergone angioplasty or endartarectomy. Restenosis is believed to proceed via a process that includes both proliferation (mitosis) and migration of vascular smooth muscle cells in the area damaged by the surgical procedure.

The present invention provides methods for inhibiting vascular stenosis through the use of antibodies against basic fibroblast growth factor (basic FGF or bFGF), acidic fibroblast growth factor (acidic FGF or aFGF) and/or platelet derived growth factor (PDGF). As used herein, "vascular stenosis" denotes the partial or complete blocking of a blood vessel through intimal thickening due to cellular migration and/or mitosis. Inhibition of stenosis will be understood to include interfering with the stenotic process by reducing or preventing cell migration, cell mitosis, or both. The inventors have found that therapeutic use of anti-growth factor antibodies can inhibit vascular stenosis by reducing the migration and/or mitosis of vascular SMCs.

Antibodies useful within the present invention may be produced by conventional procedures of immunization and purification. Briefly, a purified growth factor is administered to an animal such as a mouse, rat, rabbit or goat in an amount sufficient to cause an immune response. It is preferred to administer the growth factor in combination with an adjuvant, such as Freund's adjuvant, in order to enhance the immune response. Although a single injection of growth factor may be sufficient to induce antibody production in the animal, it is generally preferred to administer a large initial injection followed by one or more booster injections over a period of several weeks to several months. See, e.g., Hurrell, J. G. R., ed., *Monoclonal Hybridoma Antibodies: Techniques and Applications*, CRC Press Inc., Boca Raton, Fla., 1982, which is incorporated herein by reference. Blood is then collected from the animal and clotted, and antibodies are isolated from the serum using conventional techniques such as salt precipitation, ion exchange chromatography, affinity chromatography or high performance liquid chromatography. Growth factors for use in immunization are prepared from natural sources or genetically engineered cells according to conventional methods such as those described by Raines and Ross (*J. Biol. Chem.* 257: 5154–5160, 1982), Antoniades (U.S. Pat. No. 4,479,896), Murray et al. (U.S. Pat. Nos. 4,801,542, 4,845,075 and 4,889,919), Bohlen et al. (*FEBS Lett.* 185: 177–181, 1985), Barr (WO 90/05184), Fiddes et al. (WO 87/01728) and Moscatelli et al. (EP 226,181), which are incorporated herein by reference. In the alternative, purified growth factors can be obtained from commercial suppliers (e.g. Genzyme Corp., Boston, Md.; Collaborative Research, Bedford, Md.).

Within one embodiment of the invention, monoclonal antibodies are used. Monoclonal antibodies provide the advantages of ease of production and lower therapeutic doses as compared to polyclonal antisera, since only antibodies of the desired specificity are used. Methods for producing monoclonal antibodies are well known in the art and are disclosed, for example, by Kohler and Milstein (*Nature* 256: 495, 1975; *Eur. J. Immunol.* 6: 511–519, 1976). See also Hurrell, J. G. R., ed., *Monoclonal Hybridoma Antibodies: Techniques and Applications*, CRC Press Inc., Boca Raton, Fla., 1982. As will be appreciated by those skilled in the art, antibody fragments, such as Fab fragments, may also be used.

It is generally preferred to use antibodies that are syngeneic with the patient or that contain syngeneic constant regions. For this reason, genetically engineered antibodies will generally be used in the treatment of humans. Methods for producing recombinant human antibodies or humanized non-human (i.e. chimeric) antibodies are disclosed by Cabilly et al. (U.S. Pat. No. 4,816,567), Robinson et al. (WO 87/02671) and Neumaier (WO 90/00616), which are incorporated herein by reference. Briefly, human constant region genes are joined to appropriate human or non-human variable region genes. The joined genes are then transfected into host cells, which are cultured according to conventional procedures. In the alternative, monoclonal antibody producing cells may be transfected with cloned human constant region genes, and chimeric antibody genes generated by homologous recombination. Thus it is possible to assemble monoclonal antibodies with a significant portion of the structure being human, thereby providing antibodies that are more suitable for multiple administrations to human patients.

Within the present invention it is preferred to use neutralizing antibodies. "Neutralizing antibody" is used herein to designate an amount of an antibody sufficient to block essentially all of the biological activity of an antigen in an in vitro test system. Suitable in Vitro test systems include, inter alia, mitogenesis assays and receptor binding assays. For example, 200 µg/ml of a polyclonal anti-PDGF IgG described herein is able to block the mitogenic and chemotactic activity of 2 ng/ml of each of the dimeric forms of PDGF. As will be understood by those skilled in the art, the amount of antibody needed to neutralize a given amount of antigen will depend on such factors as antibody specificity and affinity.

Because PDGF is a mixture of the three possible dimer combinations (isoforms) of its component chains (known as A-chain and B-chain), the anti-PDGF antibodies used within the present invention will preferably be a panel of antibodies capable of neutralizing all three isoforms (AA, BB and AB). Monoclonal antibodies are preferred. Methods of making isoform-specific anti-PDGF monoclonal antibodies are disclosed by Hart et al. (U.S. patent application Ser. No. 07/139,960; Biochemistry 29: 166–172, 1990). Hybridomas producing isoform-specific anti-PDGF monoclonal antibodies have been deposited on Dec. 17, 1987 with the American Type Culture Collection 12301 Parklawn Drive, Rockville, Md. 20852 under accession numbers HB 9610, HB 9611, HB 9612 and HB 9613.

Anti-FGF and anti-PDGF antibodies may be administered in combination or in overlapping or sequential schedules. When used in combination, the antibodies will generally be administered prior to surgery and continuing after surgery at intervals of from several hours to several days over the course of one to two weeks or more. In many cases it will be preferable to administer daily doses during a hospital stay, followed by less frequent bolus injections during a period of outpatient treatment. In the alternative, an anti-FGF antibody is administered prior to surgery, either alone or in combination with anti-PDGF antibody, and the patient is treated as described above with anti-PDGF antibody following surgery.

Doses of antibody will be selected on the basis of neutralization criteria as described above. Dosage levels are calculated from neutralization data after determining clearance of antibody from the blood. In general, dosage is selected with the goal of maintaining circulating levels of antibody sufficient to neutralize any released growth factors. In general, doses will be in the range of about 20 µg to 500 mg or more of antibody per kg of patient body weight, preferably about 0.1 mg to 20 mg/kg, more preferably about 1 mg–10 mg/kg. Somewhat higher doses may be required if two or more antibodies are administered in combination.

For use within the present invention, anti-growth factor antibodies are formulated into injectable compositions according to conventional procedures and packaged in sterile containers. The antibodies may be combined with a suitable diluent such as sterile saline or sterile water. The antibody compositions may further contain carriers, stabilizers and excipients such as sugars (e.g. mannitol) or albumin. In the alternative, the antibodies may be provided in lyophilized form and reconstituted in a suitable diluent prior to use. These compositions may be packaged in single or multiple dosage form, for example in sealed ampoules or vials. Packages may contain one antibody, a mixture of antibodies (e.g. anti-PDGF and anti-bFGF) or combinations of individual antibodies in separate containers or compartments.

For inhibition of stenosis in vascular grafts, anti-growth factor antibodies are covalently attached to the graft through their constant regions or incorporated into the graft in slow-release formulations.

The following examples are offered by way of illustration, not by way of limitation.

EXAMPLES

Example 1

Female New Zealand rabbits (3 kg body weight) were immunized with recombinant human bFGF (pharmaceutical grade; obtained from Synergen, Inc., Boulder, Colo.). Immunization was by intradermal injection of 120 µg of bFGF in combination with Freund's adjuvant (Sigma Chemical Co., St. Louis, Mo.). A booster immunization (60 µg of bFGF intradermally) was given three weeks later, and immune serum was obtained five weeks after the first immunization. The IgG fraction of the immune serum was obtained by chromatography using Protein G Sepharose (Pharmacia LKB, Uppsala, Sweden). Pre-immune serum was obtained from the rabbits prior to immunization.

The specificity of the anti-bFGF IgG was tested in a mitogenesis assay on 3T3-D1 cells (a subclone of Swiss mouse 3T3 fibroblasts). The cells were plated at a density of $4 \times 10^4$ cells/well in a 24-well tray in Dulbecco's modified Eagle's medium supplemented with 10% calf serum. After three days, the cells reached confluence and were made quiescent by incubation in medium containing 0.5% calf serum for an additional two days. Recombinant PDGF-BB (prepared in yeast essentially as disclosed by Murray et al., U.S. Pat. No. 4,845,075, incorporated herein by reference), EGF (culture grade; obtained from Collaborative Research, Bedford, Md.) and bFGF were preincubated for 10 minutes at 37° C. with either 100 µg/ml of anti-bFGF IgG or preimmune IgG. The quiescent cells were then incubated in the presence of 5 ng of growth factor or 5% calf serum for 20 hours. [$^3$H]-thymidine (6.7 mCi/mmol, DuPont-New England Nuclear) incorporation into DNA of the cells (1 µCi/ml, $1 \times 10^5$ cells/well) was measured in a liquid scintillation counter following a two hour pulse. As shown in FIG. 1, the anti-bFGF IgG neutralized the mitogenic effect of bFGF but did not significantly reduce the mitogenic response to PDGF, EGF or calf serum. The antibody also showed no cross-reactivity with acidic fibroblast growth factor in an immunoblot assay and had no effect on the initial platelet adherence to denuded arteries.

Male Sprague-Dawley rats (3.5 months old, 350–400 grams body weight) were obtained from Tyler Laboratories (Bellevue, Wash.). The animals were anesthetised with an initial intramuscular injection of 0.06 mg/kg fentanyl (Innovar-Vet, Pitman-Moore, Mundelien, Ill.) and additional injections when necessary. The distal left common and external carotid arteries were exposed through a midline wound in the neck. The endothelium was removed from the left common carotid artery using a filament loop essentially as described by Fingerle et al. (*Arteriosclerosis* 10: 1082, 1990) and Lindner et al. (*Lab. Invest.* 61: 556, 1989). The monofilament suture loop was introduced into the left external carotid artery via a trocar made of polyethylene tubing. The device was pushed through the trocar into the common carotid, then steadily pulled back along the carotid with constant rotation. Anti-bFGF antibody (10 mg/animal) was administered via the tail vein. Five minutes after denudation with the filament loop, balloon catheter denudation of the same artery was carried out essentially as described by Clowes et al. (*Lab. Invest.* 49: 327, 1983). A 2 French balloon catheter was introduced through the external carotid artery and passed through the common carotid three times with the balloon distended sufficiently with saline to generate slight resistance and produce distension of the carotid itself. The external carotid was ligated after removal of the catheter, and the wound was closed. After surgery, five additional intravenous injections of anti-bFGF antibody (2.5 mg/animal) were given at eight hour intervals. Control animals were treated in an identical fashion with the exception that matching concentrations of nonimmune IgG were injected at the same times.

Figure 2:
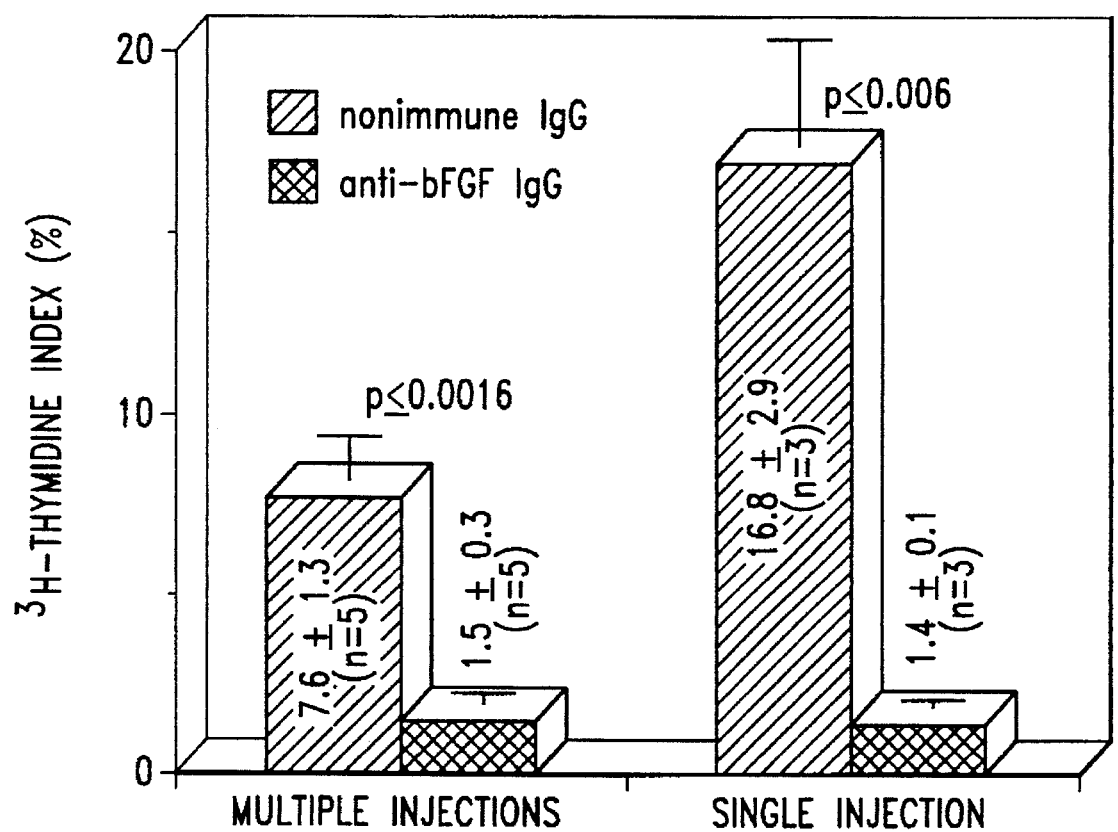
FIG. 2 illustrates the replication of medial smooth muscle cells 41 hours after balloon catheter denudation in animals treated with anti-bFGF antibody or control (nonimmune) antibody. Data represent means +/−SEM.

At 24, 32 and 40 hours after balloon catheter injury, all animals were injected with tritiated thymidine (50 µCi/100 g body weight). Forty-one hours after injury the animals were perfused-fixed. Briefly, the animals were anesthetized and killed by injection of sodium pentobarbital. A catheter was placed in the carotid artery and the animal perfused with Ringer's lactate, then fixed with 2% glutaraldehyde, 1% paraformaldehyde in cacodylate buffer at physiologic pressure for five minutes. The denuded carotid arteries were excised and further fixed by immersion in the same fixative as was used for perfusion. Tissue samples were embedded in paraffin for cross-sectioning. One-micrometer cross-sections were dipped in Kodak NTB-2 emulsion, stored at 4° C. for two weeks, and developed using Kodak D 19 developer. Under these conditions the background was negligible. The thymidine index was determined by counting cells under oil immersion. As shown in FIG. 2, the proliferation of medial SMCs was significantly reduced in those animals that received the anti-bFGF antibody (1.5% vs. 7.6% in controls).

Example 2

Balloon catheter injury was induced in rats as described in Example 1. The animals were each given a single injection of 10 mg anti-bFGF IgG or nonimmune IgG prior to surgery. Post-surgical administration of antibody was omitted. All other procedures were carried out as described in Example 1. As shown in FIG. 1, the proliferation of medial SMCs was reduced by a single injection of anti-bFGF antibody prior to injury (1.4% vs. 16.8% in controls).

Example 3

Goat antisera was raised to purified human PDGF (Raines and Ross, ibid). Six injections of approximately 75 µg were given at two-week intervals. The initial injection was in complete Freund's and subsequent injections in incomplete Freund's adjuvant. All injection were given subcutaneously at 10 to 15 sites. The first positive bleed was 3 months following the initial injection. Antibody was obtained by plasmapheresis of the animal to allow frequent collection of large amounts of antibody and to prevent release of endogenous PDGF from platelets. All of the antibody used in these studies was following the additional injection of 350 µg of PDGF which resulted in a 5–20 fold increase in serum titer. Typical titer of the animal removed the mitgenic activity of 2 ng/ml purified PDGF on 3T3 cells at a plasma dilution of 1:320. The IgG fraction was prepared by 18% sodium sulfate precipitation of plasma followed by DEAE-Sephacel chromatography. Normal goat IgG was prepared by the same procedure. Protein concentration of both preparations was determined by the method of Lowry et al., (J. Biol. Chem. 193: 265, 1951).

Three different methods were used to evaluate the specificity of anti-PDGF antibody; immunoprecipitation of $^{125}I$-test substances, including insulin, EGF, platelet factor 4, β-thromboglobulin, FGF, TGF-β, and TGF-α; inhibition of the mitogenic activity of test samples on 3T3 cells as described in Example 1 using insulin, EGF, FGF, and IGF-1; and inhibition of PDGF competitive activity to evaluate species specificity, in which a serum concentration which resulted in approximately 75% competition in a PDGF radioreceptor assay (performed essentially as described by Bowen-Pope and Ross, Methods Enzymol. 209: 69–100, 1985) was preincubated with 400 µg/ml anti-PDGF IgG for 1 hour at 37° C. prior to addition to the 3T3 cells. Anti-PDGF only immunoprecipitated dimeric forms of PDGF and only neutralized the mitogenic activity of dimeric forms of PDGF. PDGF competitive activity in serum from humans, pigs, dog, horse, mouse, rat, chicken, rabbit and non-human primate were completely neutralized by anti-PDGF. Only PDGF competitive activity in serum from sheep, cows and goat were not neutralized by the anti-PDGF.

A total of 38 homozygous nude rats aged 4–5 months of age (approximately 200 g weight) were obtained from the National Institutes of Health, Bethesda, Md. and housed in a pathogen-free facility. Either goat anti-PDGF or non-immune goat IgG were administered daily by IP injection starting the day before surgery. An antibody dose of 60 mg/100 g body weight was sufficient to achieve antibody levels between 1.5 and 2 mg/ml 24 hours after administration. On the day of surgery, animals were anaesthetized using ketamine and Rompun, and both common carotid arteries were balloon catheterized using a 2 French embolectomy catheter or with a teflon loop (gentle injury model) essentially as described by Fingerle et al. (Arteriosclerosis 10: 1082, 1990). Blood samples were taken during the operative procedure and at sacrifice to determine circulating blood levels of antibody in each animal. Animals were sacrificed 8 days after surgery. 17, 9 and 1 hour prior to sacrifice, animals were injected with [$^3$H]-thymidine (50 µCi/100 gm) was administered to label proliferating intimal and medial cells. At the time of sacrifice, animals were anaesthetized with ketamine and Rompun. Blood was taken for antibody levels and the animals injected with Evans Blue. After 10–15 minutes, the jugular veins were isolated for perfusion run-off with a cannula introduced into the abdominal aorta. The animals were injected with a lethal dose of sodium pentobarbital before perfusion with Ringer's Lactate and fixation in situ with 4% paraformaldehyde. Both carotids were divided into three segments so that the uniformity of the lesion could be assessed.

Initial screening of the intimal and medial cross-sectional areas of 7 non-immune and 6 anti-PDGF animals following balloon injury, and 4 non-immune and 5 anti-PDGF animals following gentle injury indicated a reduction in intimal thickening in the anti-PDGF animals, as evidenced by a lower ratio of intimal area to medial area vs. controls (non-immune IgG). Data are shown below in the Table.

TABLE

| Rat | Plasma anti-PDGF (µg/ml) | | Intimal Area: Medial Area |
|---|---|---|---|
| | d = 1 | d = 8 | Ratio |
| Balloon Injury | | | |
| +Anti-PDGF | | | |
| N1 | 1520 | >2000 | 0.14 |
| N8 | >2000 | >2000 | 0.18 |
| S2 | 1057 | 1392 | 0.28 |
| S4 | 1172 | 1457 | 0.13 |
| S10 | 1085 | 1320 | 0.22 |
| S12 | 1123 | 1285 | 0.21 |
| Mean (SE) | | | 0.19 (0.06) |
| +Non-immune IgG | | | |
| N4 | | | 0.19 |
| N5 | | | 0.29 |
| N9 | | | 0.25 |
| S5 | | | 0.28 |
| S7 | | | 0.40 |
| S8 | | | 0.44 |
| S9 | | | 0.34 |
| Mean (SE) | | | 0.31 (0.08) |
| Gentle Injury | | | |
| +Anti-PDGF | | | |
| S2 | 1057 | 1392 | 0.16 |
| S4 | 1172 | 1457 | 0.11 |
| S10 | 1085 | 1320 | 0.15 |
| S11 | 1237 | 1339 | 0.07 |
| S12 | 1123 | 1285 | 0.18 |
| Mean (SE) | | | 0.13 (0.04) |
| +Non-immune IgG | | | |
| S5 | | | 0.22 |
| S7 | | | 0.39 |
| S8 | | | 0.39 |
| S9 | | | 0.24 |
| Mean (SE) | | | 0.32 (0.10) |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of reducing restenosis in a mammal following angioplasty or endartarectomy comprising administering to said mammal an anti-growth factor antibody in an amount sufficient to reduce restenosis, wherein said antibody is selected from the group consisting of anti-bFGF antibodies, anti-aFGF antibodies and anti-PDGF antibodies, and wherein said antibody inhibits the chemotactic or mitotic activity of the growth factor.

2. A method according to claim 1 wherein said antibody is a monoclonal antibody.

3. A method according to claim 1 wherein said antibody is an anti-bFGF antibody.

4. A method according to claim 1 wherein said antibody is an anti-PDGF antibody.

5. A method according to claim 1 wherein said antibody is administered prior to angioplasty or endartarectomy.

6. A method according to claim 1 wherein said antibody is administered subsequent to angioplasty or endartarectomy.

7. A method according to claim 1 wherein a panel of anti-growth factor antibodies is administered to said animal.

8. A method according to claim 7 wherein said panel of anti-growth factor antibodies comprises neutralizing antibodies to the AA, AB and BB isoforms of PDGF.

9. A method according to claim 7 wherein said panel of anti-growth factor antibodies comprises anti-bFGF antibodies and anti-PDGF antibodies.

10. A method of reducing restenosis in a mammal following angioplasty or endartarectomy comprising:

administering to said mammal prior to angioplasty or endartarectomy an anti-FGF antibody in an amount sufficient to reduce restenosis; and administering to said mammal following angioplasty or endarterectomy an anti-PDGF antibody in an amount sufficient to reduce restenosis.

11. A method according to claim 10 wherein said antibodies are monoclonal antibodies.

12. A method according to claim 10 wherein said anti-FGF antibody is an anti-bFGF antibody.

13. A method according to claim 10 wherein a panel of anti-PDGF antibodies is administered.

14. A method according to claim 13 wherein said panel of antibodies comprises neutralizing antibodies to the AA, AB and BB isoforms of PDGF.

15. A method according to claim 10, further comprising administering to said mammal prior to angioplasty or endartarectomy an anti-PDGF antibody in an amount sufficient to reduce restenosis.

16. A method of reducing vascular stenosis in a mammal comprising administering to said mammal an anti-growth factor antibody in an amount sufficient to inhibit mitogenesis and/or migration of vascular smooth muscle cells, wherein said antibody is selected from the group consisting of anti-bFGF antibodies, anti-aFGF antibodies and anti-PDGF antibodies.

17. A method according to claim 16 wherein said antibody is a monoclonal antibody.

18. A method according to claim 16, wherein said antibody is an anti-bFGF antibody.

19. A method according to claim 16 wherein said antibody is an anti-PDGF antibody.

20. A method according to claim 16 wherein a panel of anti-growth factor antibodies is administered to said animal.

* * * * *